US006814867B2

(12) United States Patent
Fodor et al.

(10) Patent No.: US 6,814,867 B2
(45) Date of Patent: Nov. 9, 2004

(54) PROCESS FOR REDUCING CHROMIUM IN NONVOLATILE RESIDUE RESULTING FROM AIR OXIDATION OF CYCLOHEXANE

(75) Inventors: Ludovic Fodor, Beaumont, TX (US); Bennett Haines Novak, Orange, TX (US); Jules Charles Joseph Perilloux, Jr., Beaumont, TX (US); Bhagya Chandra Sutradhar, Wilmington, DE (US)

(73) Assignee: Inuista North America S.à.r.l.

( * ) Notice: Subject to any disclaimer, the term of this patent is extended or adjusted under 35 U.S.C. 154(b) by 135 days.

(21) Appl. No.: 10/242,546

(22) Filed: Sep. 12, 2002

(65) Prior Publication Data
US 2004/0050780 A1 Mar. 18, 2004

(51) Int. Cl.[7] .............................................. B01D 11/04
(52) U.S. Cl. ....................... 210/634; 210/774; 210/913; 568/342; 568/835; 568/836
(58) Field of Search .................... 210/634, 639, 210/757, 774, 800, 804, 913; 422/258; 568/342, 344, 832, 835–837

(56) References Cited

U.S. PATENT DOCUMENTS

| 4,465,861 A | * | 8/1984 | Hermolin .................... 568/342 |
| 4,720,592 A | | 1/1988 | Besmar et al. |
| 5,308,501 A | | 5/1994 | Eckert |
| 5,932,109 A | * | 8/1999 | Griffin ........................ 210/709 |
| 6,008,415 A | * | 12/1999 | Greene et al. .............. 568/358 |
| 6,515,171 B1 | * | 2/2003 | Hirai ........................ 562/512.4 |
| 6,563,001 B1 | * | 5/2003 | Costantini et al. .......... 562/543 |
| 6,703,529 B1 | * | 3/2004 | Fodor et al. ................ 568/342 |
| 2002/0042722 A1 | | 4/2002 | Tsuji et al. |

FOREIGN PATENT DOCUMENTS

| DE | 4336225 | 10/1993 |
| JP | 5775186 | 5/1982 |
| WO | WO 9914179 | 3/1999 |

OTHER PUBLICATIONS

PGPUBS Document, Fache, US2003/0166967, Published Sep. 4, 2003, Effective Filing Date Sep. 4, 2002.*

* cited by examiner

Primary Examiner—Joseph Drodge

(57) ABSTRACT

Disclosed herein is a process for reducing or substantially eliminating chromium in non-volatile residue obtained from a certain processes, and particularly from cyclohexane oxidation processes.

28 Claims, 2 Drawing Sheets

PROCESS FOR REDUCING CHROMIUM IN NONVOLATILE RESIDUE RESULTING FROM AIR OXIDATION OF CYCLOHEXANE

FIELD OF THE INVENTION

The present invention relates to methods for reducing the amount of chromium present in non-volatile residue (NVR). More specifically, the invention relates to methods for reducing the amount of chromium present in non-volatile residue obtained during the production of cyclohexanol and cyclohexanone by air oxidation of cyclohexane.

BACKGROUND OF THE INVENTION

Non-volatile residue ("NVR"), obtained during the production of cyclohexanol and cyclohexanone by air oxidation of cyclohexane, is an aqueous mixture of organic and inorganic compounds comprising butyric acid, valeric acid, caproic acid, 6-hydroxy-caproic acid, glutaric acid, succinic acid, adipic acid, oligomers of one or more of these organic compounds, organic esters of phosphoric acid, including diethylhexyl phosphoric acid (DEHPA), chromium compounds, including chromium complexes involving the above compounds, and water.

NVR of the above type is produced as waste stream in cyclohexane oxidation processes and is generally disposed of as boiler fuel. Combustion of NVR in a boiler might cause emission of chromium with boiler stack gases. Expensive stack gas treatment is required in order to maintain an acceptable low concentration of chromium in the stack gas. Alternative routes of disposal of NVR are also expensive.

It is, therefore, desirable to have a method to significantly reduce the amount of chromium in NVR so that, upon combustion, it will produce a stack gas with an acceptable low concentration of chromium. It is also desirable to have a method for reducing chromium content of NVR in a way that its organic content is not substantially reduced. In other words, a new waste organic content stream should not be created.

Techniques available in the art for reducing the concentration of chromium in aqueous waste products involve reduction of hexavalent chromium to trivalent chromium using a suitable reducing agent and precipitation of trivalent chromium using a suitable precipitant. A two-step process is described in U.S. Pat. No. 5,308,501 for treating heavy metal solutions with ferrous sulfate and caustic to precipitate chromium as chromium hydroxide. In JP 57075186 chromium and fluorine is removed from waste water by reducing the hexavalent chromium to trivalent chromium with ferrous sulfate, sodium sulfite or sodium bisulfite and adding calcium hydroxide until chromium is precipitated.

It is well known in the art that phosphoric acid, DEHPA and organic dicarboxylic acids form strong complexes with chromium. No method is available for precipitating chromium in the presence of complexing agents, such as organic dicarboxylic acids and DEHPA.

WO 9914179 describes a method for recovering catalyst from a mixture of catalyst and water obtained from hydrocarbon oxidation. The method used reduction of the temperature, or distilling off amounts of water, or both. For NVR, cooling or evaporating portion of water cause solidification of some of the organic compounds.

U.S. Pat. No. 4,720,592 teaches that catalysts and additives that may be used during the cyclohexane oxidation process may also end up in the NVR.

US 2002042722 teaches in-situ treatment of an underground area containing hexavalent chromium and other metals. The in-situ treatment and remediation of an underground area comprises the use of ferrous sulfate and acid such as sulfuric acid or phosphoric acid, as the first reactive solution to de-complex chromium and initiate reduction of hexavalent chromium to trivalent chromium. A second reactive solution comprising of hydrogen peroxide and acid destroys organic ligands.

DE 4336225 describes a method for toxic chromate removal from heat-storage bricks. The method uses ferrous sulfate in sulfuric acid to reduce the hexavalent chromium to trivalent chromium. The method of the present invention does not require the reduction of hexavalent chromium to trivalent chromium.

U.S. Pat. No. 5,308,501 describes a two-step process for treating heavy metal solutions with ferrous sulfate and caustic to precipitate chromium as chromium hydroxide. The process does not decompose the chromium ligands.

There are many shortcomings to the methods that are described in the art. When the chromium catalyst level is in the tenths to hundredths ppm range, the chromium will not precipitate at low temperatures. If the water is distilled off, the organic components in NVR will precipitate rather than the desired chromium. Because of the complex composition and physical properties of NVR none of the above methods work to reduce or substantially eliminate chromium in NVR.

The object of the present invention is to provide a method for reducing or substantially eliminate the amount of chromium, while eliminating the step of reducing hexavalent chromium to trivalent chromium.

BRIEF DESCRIPTION OF THE DRAWINGS

The figures are presented to aid in the understanding of the present invention.

SUMMARY OF THE INVENTION

Figure 1:
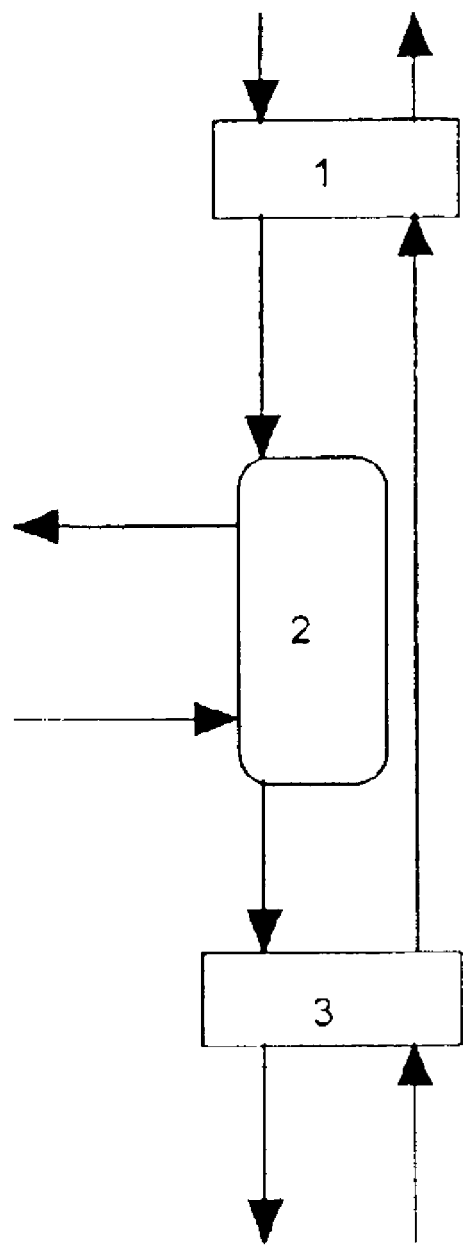
FIG. 1 is schematic diagram the general process of one embodiment of the present invention. The NVR is contacted with electrolyte solution (1) to remove water-extractable chromium. The NVR is then hydrolyzed using dilute mineral acid solution (2). The hydrolyzed NVR may be contacted with fresh electrolyte solution (3). The resulting NVR is low in chromium concentration and may be used as fuel.
Figure 2:
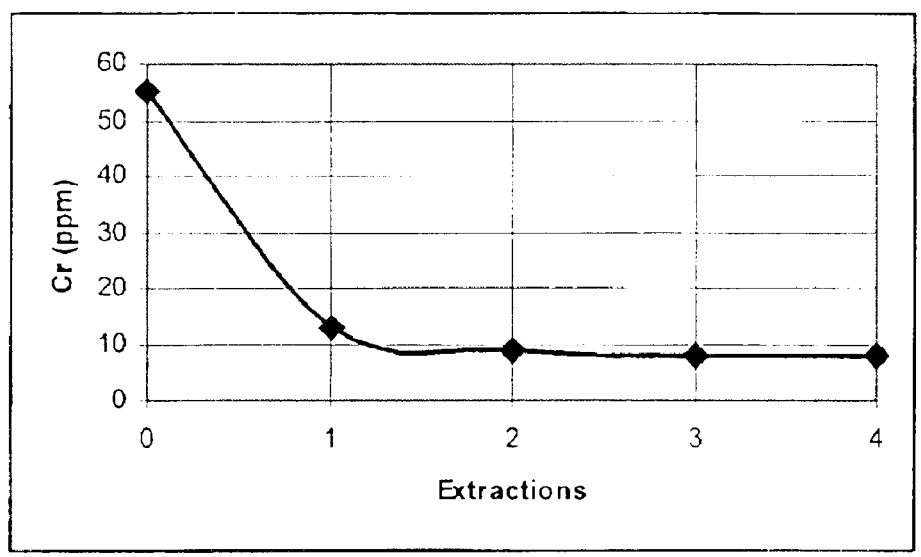
FIG. 2 illustrates the reduction of chromium, in parts per million, in NVR by extraction steps only.

Disclosed herein is a process to separate chromium from non-volatile residue, said process comprising contacting the non-volatile residue with an aqueous electrolyte solution, followed by separation of the aqueous phase from the organic phase, and, optionally, repeating the steps.

A process for hydrolyzing/decomposing chromium-containing compounds in non-volatile residue comprising reacting non-volatile residue with an acidic compound.

Another disclosure is a process for reduction of chromium content in non-volatile residue from a cyclohexane oxidation process, said process comprising, (a) contacting the non-volatile residue with an aqueous electrolyte solution followed by separation of the aqueous phase from the organic phase and (b) reacting the non-volatile from step (a) with an acidic compound.

DETAILED DESCRIPTION OF THE INVENTION

The present invention is a process for reducing or substantially eliminating the amount of chromium in nonvolatile residue ("NVR"). One embodiment of the present invention is a process for reducing or substantially eliminating the amount of chromium in non-volatile residue ("NVR"), that is obtained from the air oxidation of cyclohexane. The resulting low-chromium contain may be used as fuel.

NVR from cyclohexane oxidation processes may comprise butyric acid, valeric acid, caproic acid, 6-hydroxycaproic acid, glutaric acid, succinic acid, adipic acid, oligomers of one or more of these organic compounds, organic esters of phosphoric acid, including diethylhexyl phosphoric acid (DEHPA), or chromium compounds, including chromium complexes involving the above compounds, and water.

NVR and water are significantly miscible. Therefore, the process of the present invention utilizes an aqueous electrolyte extraction solution for reducing the amount of chromium in non-volatile residue. The step of reducing hexavalent chromium to trivalent chromium is not needed.

In the method of the present invention, at least a portion of the chromium complexes that are present in the NVR are hydrolyzed using dilute acid solution. Such hydrolysis facilitates the extraction of chromium by aqueous electrolyte.

Presence of electrolyte in the aqueous phase surprisingly reduces the dissolution of organic compounds in the aqueous phase. At the same time, the presence of electrolyte in the aqueous phase increases the partitioning of chromium towards the aqueous phase despite the presence of several complexing agents, such as DEHPA, in NVR that normally facilitate partitioning of chromium towards the organic phase.

Electrolytes that are suitable for the present invention include, but are not limited to, $MgSO_4$, $FeCl_3$, $Al_2(SO_4)_3$, $FeSO_4$, $Na_2SO_4$, $K_2SO_4$, $(NH_4)_2SO_4$, $CuSO_4$ and mixtures thereof. Nitrates, carbonates, and chlorides of the cations of the above electrolytes can also be used.

The amount of the aqueous electrolyte solution is important for the extraction. The aqueous electrolyte solution should comprise from 5 to about 50 wt % of the electrolyte salt. For example, 35 wt % $FeSO_4$, or 35 wt % $MgSO_4$ may be used.

If extractions are carried out using only electrolyte solutions, it is difficult to extract near 100% of the chromium from the NVR, as demonstrated in Table 1.

In the experiments conducted for the present invention, it was discovered that the residual chromium content of NVR (after extraction using aqueous electrolyte), is transformed to extractable form by treatment, such as hydrolysis, with dilute acid solution. Several combinations of multiple extraction steps and multiple hydrolysis steps were found to reduce the chromium content of NVR to ~1 ppm. For combustion of NVR containing a low concentration of chromium, stack gases contain acceptable low concentrations of chromium.

Also, disclosed herein is a process to separate chromium from non-volatile residue resulting from a cyclohexane oxidation process, said process comprising contacting the non-volatile residue with an aqueous electrolyte solution, followed by separation of the aqueous phase from the organic phase, and optionally repeating the steps. Separation can be accomplished by decantation.

Another embodiment of the process of the present invention is the hydrolysis/decomposition of chromium complexes in NVR. Since the chromium salts in NVR are both organic and inorganic ones, in order to reduce most or substantially all of the Cr from the NVR, the organic chromium salts (for example, chromium octoate) and Cr complexes need to be hydrolyzed to water soluble Cr salts. The hydrolysis can be accomplished by using diluted acids at temperatures from about 60° C. to about 170° C., preferably from about 80° C. to about 100° C. After the hydrolysis step, the NVR is further extracted with aqueous electrolyte solutions.

The acids and acid compounds that are suitable in the present invention are sulfuric acid, phosphoric acid, and solid acid catalysts, such as Nafion®, for example. By dilute acids, we mean acid solutions of about 0.1 to about 10 wt %, preferably from about 0.2 to about 5 wt %.

The hydrolysis can be more effective if the hydrolysis step can be done early in the process after the first or second extraction step. The process improves the reduction or removal of the chromium if the extractions are repeated.

EXAMPLES

In the Examples below, after the two separable phases were separated, the samples were analyzed for Cr using Inductively Coupled Plasma (ICP), IRIS model from the Thermo Jarrel Ash Corporation.

Comparative Example A

NVR (200 g) was vigorously mixed with 20 g of water, then transferred to a separatory funnel and left for phase separation. After standing for 24 h, separate layers were not observed. It was concluded that by using only water for extraction, it is not possible to reduce the chromium in NVR.

Example 1

Comparative example A was repeated, except that a 25 wt % $MgSO_4$ solution was used instead of water. After a short period of time, two layers were present and the lower aqueous layer was decanted. Based on the Cr analyses of the aqueous sample by ICP, 55% of the Cr from NVR was extracted into the $MgSO_4$ solution. It is possible to reduce the Cr concentration in NVR using electrolyte solution instead of water.

Example 2

Example 1 was repeated, performing 4 consecutive extractions using similar conditions. The amount of chromium removed in each step is shown in Table 1.

After 4 extractions approximately 80% of the chromium initially present in NVR was removed.

TABLE 1

|  | Number of extraction steps | | | | |
| --- | --- | --- | --- | --- | --- |
|  | 0 | 1 | 2 | 3 | 4 |
| ppm Cr remaining in NVR | 50 | 13 | 9 | 8 | 8 |

Example 3

In order to eliminate all or almost all the Cr from NVR, the organic chromium salts and Cr complexes were hydrolyzed to water-soluble Cr salts. In a 500 ml glass reactor, equipped with a heating mantle, magnetic stirrer, reflux condenser, and temperature control, 200 g of NVR was heated up to 100° C. and treated with 10 ml of 50 wt %-phosphoric acid. After stirring for 1 hour at 100 deg C. the NVR was cooled to room temperature and treated with electrolyte solution for Cr removal. The results are presented in Table 2. The Cr concentration is given after each step.

It was observed that by using hydrolyses step, the Cr concentration can be lowered to 1 ppm in NVR. By repeated extractions without hydrolysis, the Cr concentration was only lowered to 8 ppm.

TABLE 2

| | Operation steps | | | | |
|---|---|---|---|---|---|
| | Initial | Extr. −1 | Hydrolysis | Extr. −2 | Extr. −3 |
| ppm Cr remaining in NVR | 55 | 13 | 5 | 4 | 1 |

Example 4

In a 1000 mL flask equipped with a condenser, heating mantle, temperature controller, and magnetic stirrer, 500 g of NVR & 50 g of a 25 wt % $MgSO_4$ solution was heated to 100 deg C. At 100° C. the solution settled and the two layers were separated. To the NVR layer a 10% mineral acid solution was added and the contents were heated under reflux for 1 hour. After cooling 50 g of the 25 wt % $MgSO_4$ solution was added and the contents were heated to 100° C. After the solution settled and the layers were separated the extraction process was repeated one more time. The final Cr level in NVR was 1 ppm.

What is claimed is:

1. A process to separate chromium from non-volatile residue, said process comprising creating a composition comprising an organic phase and an aqueous phase by contacting chromium-containing non-volatile residue with an aqueous electrolyte solution, wherein chromium is extracted from the non-volatile residue into the aqueous phase, followed by separation of the aqueous phase from the organic phase, and, optionally, repeating the steps.

2. The process of claim 1 wherein said process is carried out in a mixer-settler.

3. The process of claim 1 wherein the electrolyte of the aqueous electrolyte solution is selected from the group consisting of $MgSO_4$, $FeCl_3$, $A_2(SO4)_3$, $FeSO_4$ $Na_2SO_4$, $K_2SO_4$, $(NH_4)_2SO_4$, $CuSO_4$, nitrates of Mg, Fe, AL, Na, K, $NH_4$ or Cu cations, carbonates of Mg, Fe, Al, Na, K, $NH_4$ or Cu cations, chlorides of Mg, Fe, Al, Na, K, $NH_4$ or Cu cations, and mixtures thereof.

4. The process of claim 1 in which the aqueous electrolyte solution comprises $MgSO_4$ or $FeSO_4$.

5. The process of claim 1 wherein the separation is done by decantation.

6. The process of claim 4 wherein the aqueous electrolyte solution comprises from about 5 wt % to about 35 wt % of $MgSO_4$.

7. The process of claim 4 wherein the aqueous electrolyte solution comprises from about 15 wt % to about 25 wt % of $MgSO_4$.

8. The process of claim 4 wherein the process is carried out at a temperature of about 20° C. to 120° C.

9. The process of claim 4 wherein the process is carried out at a temperature of about 80° C. to 100° C.

10. The process of claim 1 wherein the process is run in continuous mode.

11. The process of claim 10 wherein the non-volatile residue is in contact with the aqueous electrolyte solution from about 2 minutes up to about 60 minutes.

12. The process of claim 10 wherein the non-volatile residue is in contact with the aqueous electrolyte solution from about 5 minutes to about 40 minutes.

13. The process of claim 1 further comprising using the organic phase as fuel.

14. A process for hydrolyzing/decomposing chromium-containing compounds in non-volatile residue from an oxidation reaction comprising reacting non-volatile residue comprising chromium compounds with an acidic compound to create water soluble chromium salts.

15. The process according to claim 14 wherein the non-volatile residue is obtained from a cyclohexane oxidation process.

16. The process of claim 14 wherein the acidic compound is selected from the group consisting of 0.01–10 wt % dilute sulfuric acid, 0.01–10 wt % dilute phosphoric acid and solid acid.

17. The process of claim 14 wherein the acidic compound is selected from the group consisting of 0.2 to 5 wt % dilute sulfuric acid, 0.2 to 5 wt. % dilute phosphoric acid, and solid acid.

18. The process of claim 14 wherein the process is repeated at least once.

19. The process of claim 14 in which the temperature of operation is about 60° C. to about 170° C.

20. A process for reduction of chromium content in non-volatile residue, said process comprising,
    (a) creating a composition comprising an organic phase and an aqueous phase by contacting non-volatile residue comprising chromium with an aqueous electrolyte solution, the organic phase comprising a non-volatile residue having a reduced amount of chromium and the aqueous phase comprising chromium, followed by separation of the aqueous phase from the organic phase and
    (b) reacting the non-volatile residue of the organic phase with an aquatic compound.

21. The process of claim 20 wherein (a) is repeated at least once.

22. The process of claim 20 wherein the non-volatile residue is obtained from a cyclohexane oxidation process.

23. The process of claim 20 wherein (a) is carried out in a mixer/settler.

24. The process of claim 21, comprising repeating at least one of (a) and (b) until the non-volatile residue of the organic phase comprises a chromium content equal to or less than about 1 ppm.

25. A process to reduce chromium from non-volatile residue produced by an oxidation reaction of an organic compound, the process comprising:
    creating a first composition having an organic phase comprising non-volatile residue and an aqueous phase comprising chromium by contacting non-volatile residue comprising chromium with a first aqueous electrolyte solution;
    separating the organic phase from the aqueous phase, wherein the organic phase comprises non-volatile residue having a reduced level of chromium;
    hydrolyzing chromium compounds in the non-volatile residue with a dilute acid solution;
    contacting the organic phase with a second aqueous electrolyte solution to create a second composition comprising an organic phase comprising non-volatile residue having a further reduced level of chromium and an aqueous phase comprising chromium; and
    separating the organic phase of the second composition from the aqueous phase of the second composition.

26. The process of claim 25 wherein the first aqueous electrolyte solution is the same composition as the second aqueous electrolyte solution.

27. The process of claim 25 wherein the non-volatile residue further comprises at least one carboxylic acid.

28. The process of claim 25 wherein the chromium separated from the non-volatile residue comprises hexavalent chromium.

* * * * *